United States Patent [19]

Schuman

[11] Patent Number: 5,333,603
[45] Date of Patent: Aug. 2, 1994

[54] ENDOSCOPE WITH PALM REST

[76] Inventor: Daniel Schuman, 3790 Kings Way, Boca Raton, Fla. 33434

[21] Appl. No.: 994,730

[22] Filed: Dec. 22, 1992

Related U.S. Application Data

[62] Division of Ser. No. 841,053, Feb. 25, 1992, abandoned.

[51] Int. Cl.$^5$ .............................................. A61B 1/30
[52] U.S. Cl. ............................................ 128/7; 128/4
[58] Field of Search ............................... 128/4 A, 4, 7; 74/551.9

[56] References Cited

U.S. PATENT DOCUMENTS

| | | | |
|---|---|---|---|
| 4,408,598 | 10/1983 | Ueda | 128/4 A |
| 4,557,255 | 12/1985 | Goodman | 128/7 |
| 4,566,437 | 1/1986 | Yamaguchi | 128/4 |
| 4,572,163 | 2/1986 | Collins et al. | 128/4 |
| 4,606,330 | 8/1986 | Bonnet | 128/7 |
| 4,617,915 | 10/1986 | Arakawa | 128/4 |
| 4,881,523 | 11/1989 | Heckele | 128/4 |
| 5,159,851 | 11/1992 | Rahmes | 74/551.9 |

OTHER PUBLICATIONS

Richard Wolf Medical Instruments Corp–Operative/Diagnostic Sinuscopy brochure 111-88.
Richard Wolf Medical Instruments Corp–Panoview brochure XX-88.
ICU Medical, Inc. Lopez Valve.

Primary Examiner—Richard J. Apley
Assistant Examiner—Beverly A. Meindl
Attorney, Agent, or Firm—Cesarano & Kain

[57] ABSTRACT

One endoscopic surgical tool is used in conjunction with a laser that is powered through a small diameter laser power tube. The tool includes a bendable, rigid tube having a lumen sufficiently larger than the laser power tube such that upon application of an axial, inboard directed force, the laser power tube is axially compressed within the lumen of the bendable tube. The tool further includes a coupling tube which provides suction through the lumen of the bendable, rigid tube. Further enhancements of this tool include an axial movable, soft touch casing surrounding the tube. The tool may include a handle at the proximal end of the tube and a branch coupler and second bendable, rigid tube with suction control valves for the primary bendable tube and the branch bendable tube. Another endoscopic tool is an endoscope that includes a palm sized enclosure at a proximal end region of a stem of the endoscopic, a form-fitted palm rest attached to the bottom of the enclosure and flow control valves controlling suction and irrigation. These flow control valves have operator interface controls protruding from the top of the palm sized enclosure such that the endoscope is configured as having trumpet-like controls. Further enhancements of the endoscope include a suction control valve that is biased closed and an operator interface control that is biased upward such that the surgeon/operator variably controls the flow of the suction dependent upon the depression of the operator interface control.

11 Claims, 3 Drawing Sheets

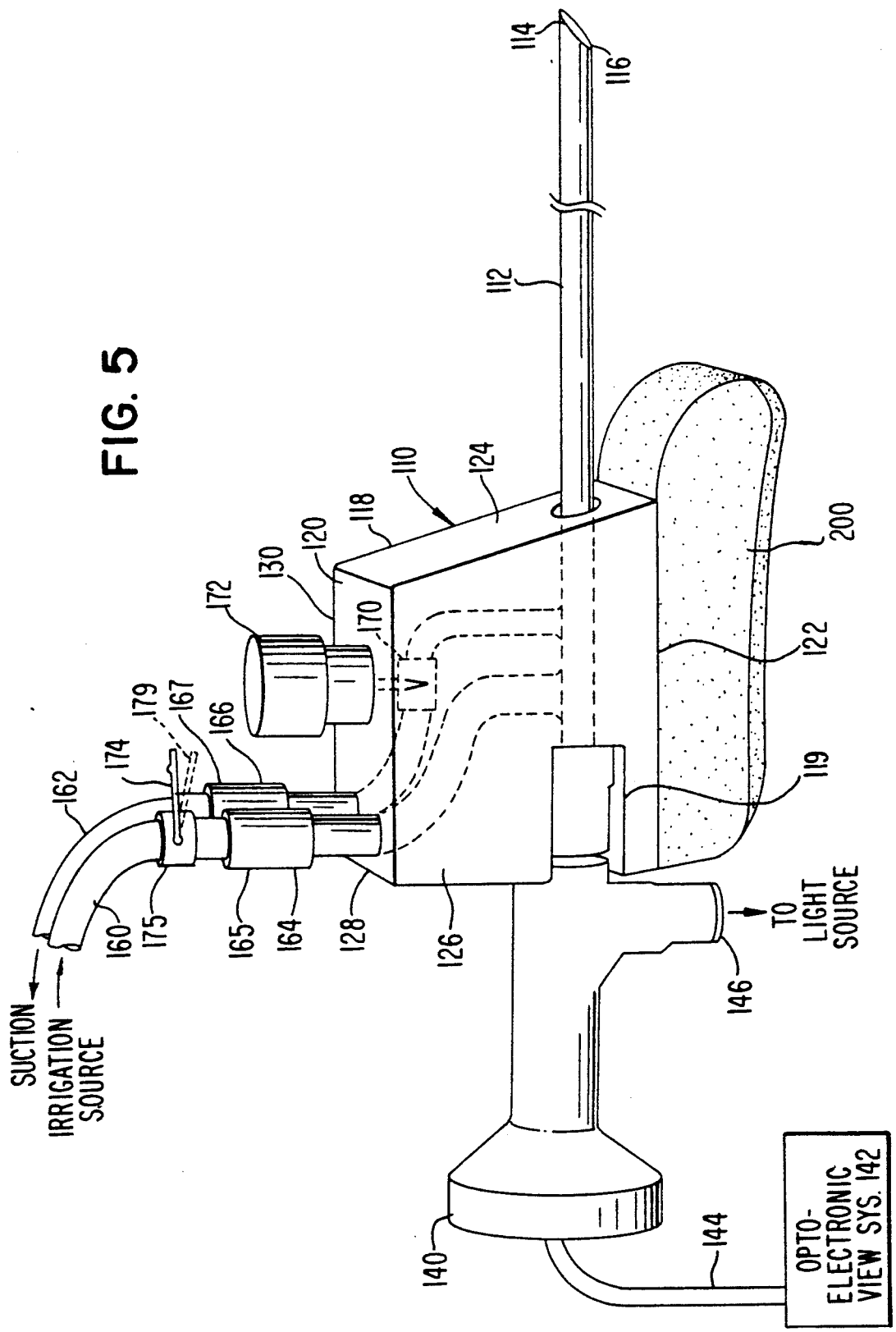

ENDOSCOPE WITH PALM REST

This is a divisional of copending application Ser. No. 07/841,053 filed on Feb. 25, 1992, now abandoned.

BACKGROUND OF THE INVENTION

The present invention relates to endoscopic surgical tools.

Endoscopic tools are presently used in certain types of surgery, and particularly sinus surgery. In use, the surgeon inserts an endoscope into the sinus of a patient in order to view the microscopic operating field with an optical, electronic viewing system. That opto-electronic system includes an optical sensor positioned at a distal end of the stem of an endoscope. The image captured by the optical sensor is optically and electronically transferred and enhanced by electronics and is viewed by the surgeon on a monitor.

One type of endoscope is made by Richard Wolf Medical Instruments Corporation of Rosemont, Ill. This endoscope has an elongated, hollow stem, an enclosure at a proximal end of the stem opposite the distal end and a camera port extending opposite the stem from the enclosure. On the top side of the enclosure, finger holes or a finger ring are provided for insertion of the surgeon's fingers. At the bottom of the enclosure is a stiff spring control valve interface, configured as a depressible valve control, which controls the flow of irrigation fluid injected through the stem and out from the distal end of the stem. Also, the Wolf endoscope includes continuous suction through the stem and out a suction port disposed in the enclosure. Irrigation is provided via an irrigation port in the enclosure. The irrigation port and the suction port are fluidly coupled to the stem within the enclosure.

Endoscopic surgery is sometimes used to clear and remove polyps and growths and debris from the sinus cavities of a patient. Sometimes, a consumable tip laser is inserted into the sinus that burns away the polyps or other nasal obstructions.

OBJECTS OF THE INVENTION

It is an object of the present invention to provide an endoscopic surgical tool that is used in combination with a laser and wherein the laser is inserted through a lumen of a bendable, rigid tube which is inserted into the body cavity of a patient.

It is another object of the present invention to provide an endoscopic surgical tool wherein the lumen of the bendable tube is large enough such that the laser and the laser power cord (supplying power to the laser) is axially compressed with the lumen upon application of an axially aligned, inboard directed force, thereby enabling the surgeon to delicately sear the object sought to be removed in the patient's body cavity.

It is a further object of the present invention to provide an endoscopic surgical tool that continuously provides suction of fluid and debris from the operating field and through the lumen of the bendable tube.

It is another object of the present invention to provide an endoscopic surgical tool that includes an axially movable, soft touch casing about the bendable tube, thereby permitting the surgeon to axially move the casing with respect to the tube to provide exposure or coverage of the distal end of the tube through which protrudes the laser.

It is another object of the present invention to provide an endoscopic surgical tool that includes a suction tube separate and apart from the tube loosely retaining the laser and laser power tube.

It is an additional object of the present invention to provide an endoscope irrigation/suction handle having a palm rest at the bottom of a palm sized enclosure and operator interface controls protruding from the palm sized enclosure such that the endoscope has trumpet-like controls.

It is a further object of the present invention to provide an endoscope wherein control valves are provided for the suction on a continually variable basis.

BRIEF DESCRIPTION OF DRAWINGS

Further objects and advantages of the present invention can be found in the detailed description of the preferred embodiment when taken in conjunction with the accompanying drawings in which:

FIG. 5 illustrates an endoscope having a form-fitted palm rest and operator interface controls for suction and irrigation valves wherein the interface controls are configured as a trumpet-like control system;

SUMMARY OF THE INVENTION

One endoscopic surgical tool is used in conjunction with a laser that is powered through a small diameter laser power tube. The tool includes a bendable, rigid tube having a lumen sufficiently larger than the laser power tube such that upon application of an axial, inboard directed force, the laser power tube is axially compressed within the lumen of the bendable tube. The tool further includes a coupling tube which provides suction of fluid and debris from the lumen of the bendable, rigid tube. Suction is provided by a vacuum source. Further enhancements of this tool include an axial movable, soft touch casing surrounding the tube. The tool may include a handle at the proximal end of the tube and a branch or "Y" coupler and second bendable, rigid tube with control valves for the primary bendable suction tube (loosely retaining the laser) and the branch or secondary bendable suction tube. Another endoscopic tool is an endoscope that includes a palm sized enclosure at a proximal end region of a stem of the endoscope, a form-fitted palm rest attached to the bottom of the enclosure and flow control valves controlling suction and irrigation through the stem. These flow control valves have operator interface controls protruding from the top of the palm sized enclosure such that the endoscope is configured as having trumpet-like controls. Further enhancements of the endoscope include a suction control valve that is biased closed and an operator interface control that is biased upward (e.g., light touch push button) such that the surgeon/operator variably controls the degree of the suction dependent upon the depression of the operator interface control.

DETAILED DESCRIPTION OF THE PREFERRED EMBODIMENTS

Figure 1:
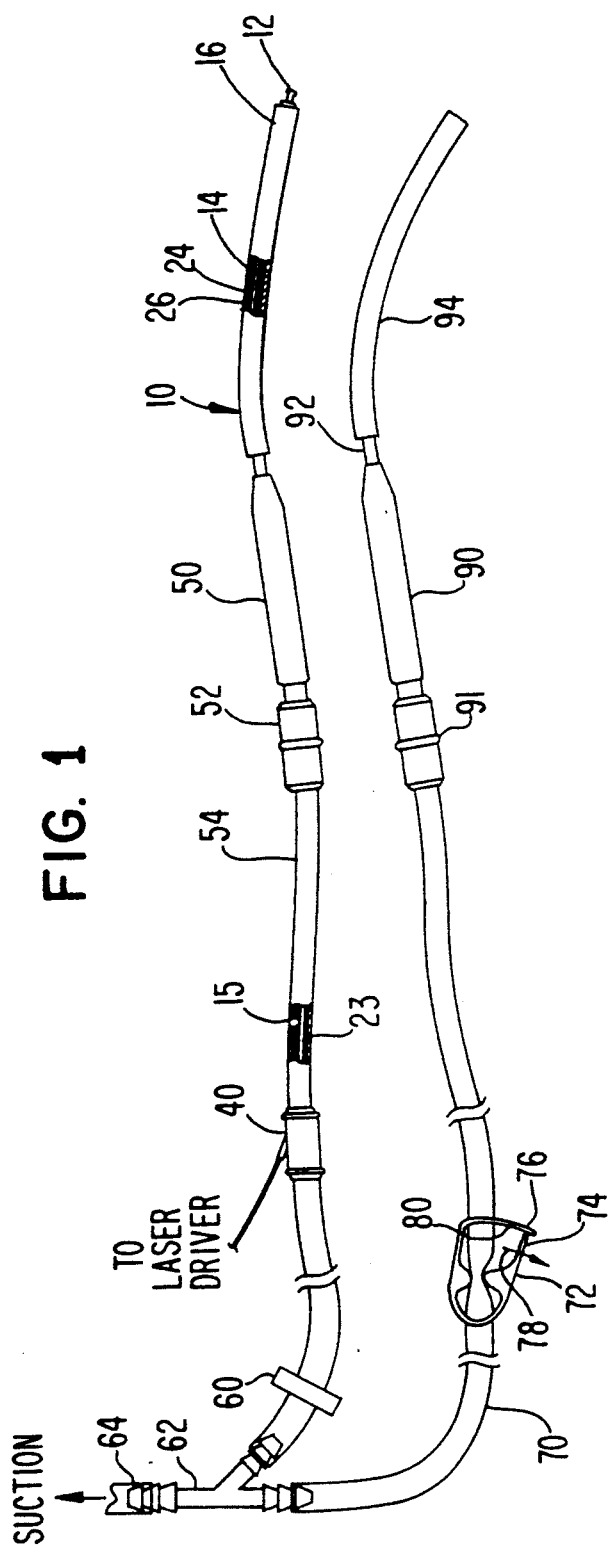
FIG. 1 illustrates an endoscopic surgical tool in accordance with the principles of the present invention and which is used in combination with a laser and a laser power tube.
Figure 2:
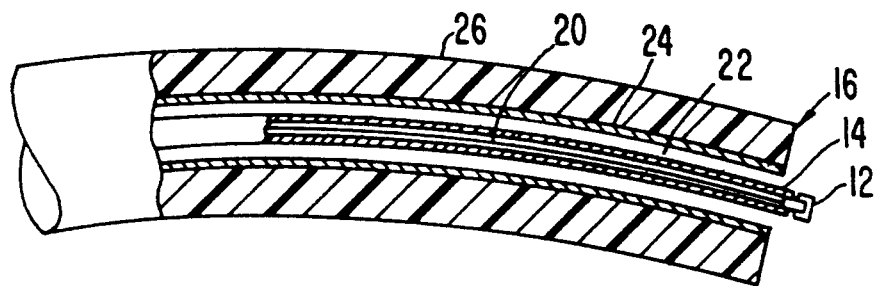
FIG. 2 illustrates an enlarged, cross-sectional view of the distal end of the rigid, bendable tube loosely retaining the laser power tube therein and which illustrates the laser tip protruding from the distal end thereof.
Figure 3:
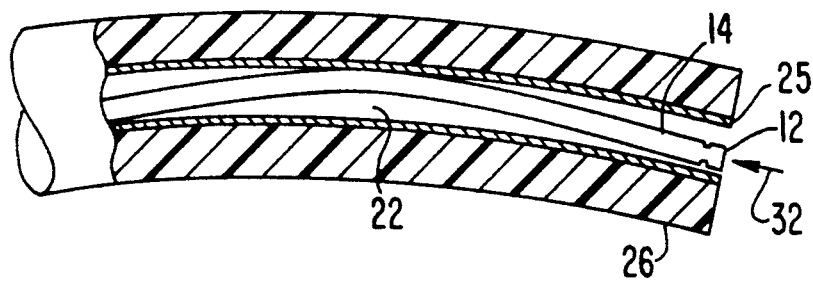
FIG. 3 illustrates an enlarged, cross-sectional view of the distal end of the rigid, bendable tube as shown in FIG. 2, wherein the laser power tube is axially compressed within the rigid, bendable tube.
Figure 4:
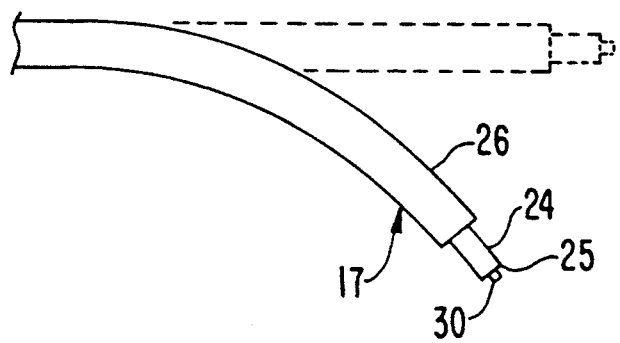
FIG. 4 diagrammatically illustrates the distal end of the rigid tube with a soft touch casing axially moved to expose the end of the rigid tube and which further illustrates how the rigid tube can be bent.

The present invention relates to endoscopic surgical tools. FIG. 1 shows a surgical tool used in conjunction with a laser. In this embodiment, the laser is a consumable tip laser having a tip 12 that is detachably connected to a laser power tube 14. FIG. 2 is an enlarged, cross-sectional view of the distal end 16 of tool 10. The consumable laser tip 12 is screwed onto laser power tube 14. In this embodiment, the outside casing of laser power tube 14 is made of a plastic or polymer and a laser feed or core 20 is inserted in the lumen of laser power tube 14. An irrigation fluid flows through the lumen of laser power tube 14 in order to cool power core 20 and irrigate the operating field. This fluid is ejected from tube 14 slightly behind tip 12. In a working embodiment, a YAG laser is utilized. The contact YAG laser is manufactured by many manufacturers. In a working embodiment, laser power tube 14 has a 2 millimeter diameter whereas laser power core 20 has a 0.6 millimeter diameter. Tip 12 has substantially the same diameter as laser power tube 14. Since blood vessels may be sized up to 2 millimeters in diameter, the size of the endoscopic tools used in microscopic laser surgery are important. Laser power tube 14 is loosely disposed or retained in lumen 22 of a bendable, rigid tube 24. In a working embodiment, bendable, rigid tube 24 is made of metal. Lumen 22 is approximately 3.5 millimeters in diameter. An axially movable, soft touch casing 26 surrounds bendable tube 24. Irrigation fluid is supplied through the lumen of power tube 14 and is generally ejected at or near the point of attachment of laser tip 12 with power tube 14. See. FIG. 2. Fluid and debris are suctioned from the operating field via lumen 22 of bendable tube 24. As shown in FIG. 4, distal end 16 of surgical tool 10 can be bent by the surgeon such that the rude, as well as the loosely retained laser tip and laser power tube, can be placed at specific locations in the body cavity of a patient during the microscopic, endoscopic surgery. As also shown in FIG. 4, soft touch casing 26 can be axially moved to expose the end 25 of bendable tube 24. In FIG. 3, tube end 25 is covered by casing 26 thereby substantially eliminating a sharp tube end which may present a problem during microscopic, endoscopic surgical procedures. Alternatively, an exposed tube end 25 as shown in FIG. 4 may, at times, be beneficial during microscopic surgery. The distal end region 30 of the consumable tip laser 12 and laser tube 14 is shown as protruding from tube 24 in FIG. 4. The dashed lines in FIG. 4 represent distal end region 17 being straightened as compared with the curved distal end region 17 shown in solid lines in that figure.

FIG. 3 shows that laser power tube 14 and hence consumable laser tip 12 can axially warp and be axially compressed within lumen 22 upon application of an axially aligned inboard directed forced shown by arrow 32 in FIG. 3. This feature of the present invention enables the surgeon to delicately conduct laser microsurgery on soft tissue without damaging the harder tissue surrounding the object being surgically removed or altered. As shown in FIG. 1, laser tube 14 extends a relatively large distance within lumen 22 (FIG. 2). FIG. 1 also shows proximal lumen region 23 and proximal laser power tube portion 15. In a working embodiment, bendable metal tube 24 is approximately 14 centimeters in length and the soft touch, axially movable casing 26 is approximately 12.5 centimeters in length. Accordingly, the soft touch casing extends over substantially all of the bendable metal tube 24. The soft touch casing enables the surgeon to insert this surgical tool into the body cavity without damage to the surrounding tissue. Also, since the consumable tip laser actually becomes hot and since bendable metal tube 24 conducts heat, the soft touch casing, which is made of a soft, resilient, rubber-like or insulative plastic, limits the distribution of heat to the surrounding tissue. The surgeon may find this helpful during the surgical procedure. If the surgeon desires to utilize the heat during the microscopic surgery, soft touch casing 26 can be axially moved to expose the end 25 of bendable metal tube 24, as shown in FIG. 4. This exposure may enable the surgeon to scrape with the end of the tube or to utilize the locally generated heat from the laser to assist in the removal of objects from the body cavity.

In a working embodiment, the distance between distal end region 16 of tool 10 and laser power tube insertion port 40 in FIG. 1 is approximately 40 centimeters. Accordingly, if an axially directed inboard force is applied to laser tip 12 (see FIG. 3, force vector 32), laser power tube 14 warps within lumen 22 along the length of the lumen between the laser tip and insertion port 40 thereby permitting reasonably significant axial compression of the laser power tube within the lumen. In a working embodiment, compression of approximately 3 millimeters has been noted.

At its proximal end, bendable tube 24 is surrounded by a handle 50. The handle is formed, in a working embodiment, in a rectilinear shape. Handle 50 also includes a hole linking the lumen of tube 24 with the ambient environment. By closing the hole, the surgeon increases the degree of suction at end 25 of tube 24. By opening the hole to the ambient environment, the degree of suction at the distal end of the tube is decreased since air is suctioned through the hole in the handle. Coupler 52 attaches an irrigation coupling tube 54 to the base of the handle. Tube 24 extends through the handle but the handle portion of the tube is not bendable. Insertion port 40 is positioned in the coupling tube and permits insertion of laser power tube 14 into the lumen of coupling tube 54 as well as lumen 22 of bendable tube 24. Insertion port 14 is fluidly sealed to limit leakage of fluid and debris passing through coupling tube 54 due to the suction therethrough. Port 14 may be pneumatically sealed to provide good suction control through tubes 54 and 24. Conventionally, laser power tube 14 is coupled to a laser driver, an irrigation source and other electronics for driving the laser, particularly to drive and cool laser tip 12.

A suction control valve 60 is disposed on coupling tube 54. Beyond control valve 60 a branch coupler 62 is attached to tube 54. A suction pump or sump is coupled to one port 64 of branch coupler 62. Branch coupler 62 provides suction for the primary coupling tube 54 and a secondary coupling tube 70. Secondary coupling tube 70 is connected to the second branch of branch coupler 62. A control device 72 is disposed on secondary coupling tube 70. In one embodiment, flow control device 72 is manufactured by Halkey Roberts Corporation of St. Petersburg, Fla. and is a plastic crimp controller which, upon depression of lever or catch arm 74 (opposite force vector 78), pinches the coupling tube thereby prohibiting suction and flow of fluid and debris through that tube. When spring loaded arm 76 is moved away from catch arm 74, arm 74 moves outboard or away from the tube pinch point as shown by arrow 78 and suction is permitted through coupling tube 70. Upon depression of operating lever catch arm 74 in a direction opposite arrow 78, the control valve pinches coupling tube 70 while lever catch arm 74 locks into one of a plurality of catch ridges on the inboard side 80 of arm 76.

The secondary coupling tube 70 is removably connected to a handle 90, via detachable coupler 91, and ultimately to a bendable, rigid metal tube 92 having a soft touch casing 94 surrounding a substantial portion thereof and particularly the distal end of the metal tube. The secondary bendable, rigid tube 92 and casing 94 is substantially the same as primary tube 24 except that the primary tube loosely retains the laser power tube therein. The soft casing on tube 92 may be axially moved to expose or cover the distal end of tube 92. Other tools can be attached to tube 70 via detachable coupler 91 by removal of handle 90 therefrom.

In operation, the surgeon using surgical tool 10 can utilize the laser while delivering irrigation fluid to the microscopic surgical field via power tube 14. Suction for the operating field is provided by the structure including primary bendable tube 24 and soft touch casing 26. The surgeon manipulates the tube by holding handle 50. The tube can be bent, the tube end can be exposed or covered and the laser tip extended outward by insertion of additional lengths of power tube 14 into port 40. Tube 14 axially compresses within tube 24 upon application of an axially directed inboard force at tip 12. If tip 12 touches a bone or hard structure in the sinus, the power tube 14 axially compresses within lumen 27. During that time, control valve 72 on secondary coupling tube 70 is closed thereby eliminating suction through the secondary surgical tool. If the surgeon desires to clean the operating field and not use the laser endoscopic tool, the surgeon closes control valve 60 on primary tube 54, removes the primary surgical tool (bendable tube 24 and soft touch casing 26) from the body cavity, inserts the secondary surgical tool (bendable tube 92 and soft touch casing 94), opens secondary branch control valve 72, thereby permitting suction through the secondary branch coupling tube 70 as well as the secondary endoscopic surgical tool.

In combination with the foregoing endoscopic surgical tool, FIG. 5 shows an improved endoscope 110. Endoscope 110 is primarily used in conjunction with surgical tool 10 for viewing endoscopic surgery, providing additional suction from the operating field and for irrigating the field. Additionally, the scope provides continuously variable suction and controlled irrigation to the microscopic operating field.

Endoscope 110 has an elongated, hollow stem 112 (sometimes called a sheath) and the stem has a lumen 114 and a distal end 116. At its proximal end, stem 112 is rotatably connected to handle enclosure 118. Handle enclosure 118 includes a top 120, a bottom 122, and four adjoining sides 124, 126, 128, and 130. Extending from back side 128 of enclosure 118 is a camera port 140. Camera port 140 may be part of the stem. Enclosure 118 has a side view port 119 that permits the surgeon to visually confirm and mechanically change the rotative position of stem 112 with respect to handle enclosure 118. The camera port is sometimes referred to as a camera ring. The port permits 360° rotation for the opto-electronic cables attached thereto. An optical electronic viewing system 142 is optically and/or electronically connected to camera port 140 via coupler line 144. A light source port 146 is adapted to be coupled to a light source. A telescope (not shown) is loosely inserted into the lumen 114 of stem 112. These basic components 112, 114, 116, 140 and 146 are present in an endoscope available from Richard Wolf Medical Instruments Corporation of Rosemont, Ill. Richard Wolf sometimes refers to this item as on axial suction-irrigation handle for an endoscope. Since the surgeon rotates the field of view, the entire end 140 of the scope rotates.

The improved endoscope, in accordance with the principles of the present invention, includes a pair of coupling hoses 160 and 162 that are respectively coupled to an irrigation source and a suction device. Accordingly, endoscope 110 includes a irrigation port 164 and a suction port 166. These ports may be configured with removable coupling attachments 165 and 167 which enable coupling hoes 160 and 162 to be removably attached and fluidly sealed to endoscope 110. Irrigation and suction ports 164 and 166 are fluidly coupled to the lumen of stem 112, as shown by dashed lines. In laser endoscopic sinus surgery, it is desirable to provide continuous irrigation via irrigation coupling tube 160 and stem 112 into the body cavity. On the other hand, it is desirable to provide controlled or variable suction through suction valve 170 and operator control interface 172 from the operating field. The flow of irrigation through irrigation coupler 160 is controlled by operator control interface 174. Continuous irrigation is desirable in order to flood the surgical field with irrigation fluid while using surgical tool 10 shown in FIGS. 1–4.

Attached to bottom 122 of enclosure 118 is a palm rest 200 which is form-fitted to rest on the base of the palm of the surgeon. Palm rest 200 is made of a material having a soft touch, i.e., latex or rubber. The height of enclosure 118, that is the distance between bottom 122 and top 120 plus the height of suction operator interface control 172, is such that the improved endoscope has trumpet-like controls. The enclosure is sized to fit in the hand of the surgeon. The fingers of the surgeon operate the trumpet-like controls by depressing suction interface control 172. Valve 170, controlling the suction, may be biased in a closed position and operator interface control 172 may be biased upward such that the surgeon must continually depress interface control 172 to provide the degree of suction from the surgical field via lumen 114.

Irrigation flow is controlled by irrigation control valve 175. Operator interface control 174 controls the flow of irrigation through lumen 114 of stem 112. The surgeon can adjust control lever 174 as shown in its dashed position 179 and thereby control the rate of flow into the operating field. This is a set-type or static control. Once the irrigation control valve is set to a certain position by the surgeon, a constant, predetermined flow of fluid is fed to the operating field via lumen 114. The surgeon need not continually depress the irrigation control valve in contrast to the suction control valve. Also, the control lever is configured as a trumpet-like control which is operated by the surgeon from the top 120 of enclosure 118. In other words, when palm rest 200 is on the base of the surgeon's palm, the surgeon's fingers can adjust the irrigation flow rate through the stem via the forward depending valve and continuously adjust the suction via a soft touch or light spring loaded push button type suction valve control.

Figure 6:
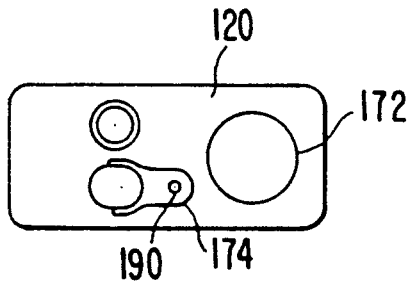
FIG. 6 diagrammatically illustrates a top view of the trumpet-like control system for the endoscope illustrated in FIG. 5.

FIG. 6 shows operator control interface 174 having a tactile sensor or bump 190 such that the surgeon can sense the irrigation flow lever by touch. The top of suction control 172 is generally flat with rounded edges because the surgeon is continuously depressing the valve.

Suction is primarily controlled by operator interface 172 since valve 170 is a variable type control which is preferably biased closed.

Figure 7:
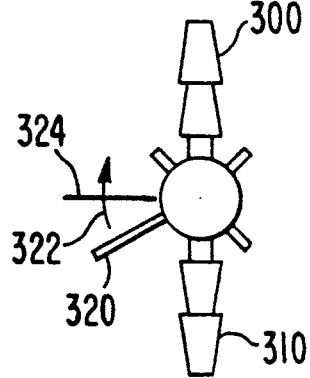
FIG. 7 illustrates a different type of flow rate valve that can be used to control the flow of irrigation fluid through the stem of the endoscope.

FIG. 7 shows a different type of set control valve which may be used with the improved endoscope. Coupler stem 310 would be attached to irrigation coupling tube 160. Coupler stem 300 would be removably attached to irrigation port 164. A static operator interface control lever 320 can be adjusted by the surgeon to various flow rate control positions, as show by arrow 322. In a working embodiment, position designated by line 324 closes the valve and angular offsets from position 324 regulate the amount of flow through the valve and hence into stem 112. The set control valve shown in FIG. 7 is available from ICU Medical, Inc. of Irvine, Calif. and is sold under the catalog number M9000. This control valve is marked with U.S. Pat. Nos. 4,790,832 and 4,895,562.

Figure 8:
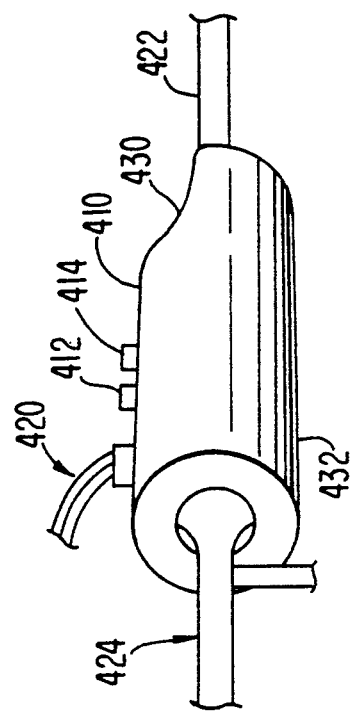
FIG. 8 illustrates a cylindrical palm grip for the endoscope.

FIG. 8 shows an alternative handle enclosure or cylindrical body 410 for the endoscope. Soft touch, push button type valve controls 412 and 414 control irrigation and suction, respectively. The diameter of cylindrical body 410 is sized to fit comfortably within the hand of the surgeon with trumpet-like controls 412 and 414 protruding from the top thereof. The top, fore-end region 430 is sloped or cut-out such that the ring finger and the pinky finger of a surgeon can rest on the sloped region. This provides a tripod hold with the thumb of the surgeon near bottom surface 432, the index and middle fingers controlling irrigation and suction and the other fingers resting on slope 430. Irrigation and suction lines 420 are removably attached to ports on the top surface region of body 410 generally axially aligned in the same plane as controls 412 and 414, that is, in a plane defined by the controls and the central axis of body 410. In the illustrated embodiment, stem 422 is co-axial with respect to the central axis of body 410. Camera and light source port connector 424 protrude from the rear of body 410. Ideally, connector 424 and stem 422 can rotate 360° with respect to body 410 with audible and mechanical position markers at predetermined intervals, such as at 10° intervals. This enables the surgeon to turn stem 422 in discrete units with respect to body 410 and rotate the field of view for the operating field.

The claims appended hereto are meant to cover modifications and changes within the spirit and scope of the present invention.

What is claimed is:

1. An endoscope having:
   a first port adapted to be coupled to an optical, electronic viewing system;
   an elongated, hollow stem having a lumen and a distal end, said distal end adapted to be inserted into a body cavity such that an optical sensor, coupled to said optical, electronic viewing system, is adapted to optically sense said body cavity;
   an irrigation port and a suction port fluidly connected to said lumen of said stem;
   wherein the improvement comprises:
   a palm sized enclosure at a proximal end region of said stem, said enclosure having a top, a bottom and four adjoining sides;
   a form-fitted palm rest attached to the bottom of the enclosure, said palm rest being shaped as a form-fitted rest for the base of a palm of an operator's hand; and,
   at least two flow control valves respectively controlling suction and irrigation and disposed between corresponding suction and irrigation ports and said stem lumen;
   respective operator interface controls, for corresponding control valves, protruding above said top of said palm sized enclosure, and said top and said operator interface controls being vertically freely accessible by at least one finger of an operator, without interference and obstruction by all other elements atop said palm sized enclosure, when said palm sized enclosure is placed in said palm of an operator;
   whereby suction and irrigation flow through said control valves is effected by actuation of said operator interface control caused by the unobstructed vertical movement of said at least one finger of said operator over said interface controls.

2. An endoscope as claimed in claim 1 wherein the suction control valve is biased in a closed position and the operator interface control is biased upward such that said operator interface control must be depressed to actuate said suction control valve.

3. An endoscope as claimed in claim 1 wherein the irrigation flow control valve can be set at predetermined flow rates based upon the positioning of the irrigation operator interface control.

4. An endoscope as claimed in claim 1 wherein the distance between the top and the bottom of said enclosure plus the height of the respective operator interface controls is such that said endoscope has trumpet-like controls.

5. An endoscope having:
   a first port adapted to be coupled to an optical, electronic viewing system;
   an elongated, hollow stem having a lumen and a distal end, said distal end adapted to be inserted into a body cavity such that an optical sensor, coupled to said optical, electronic viewing system, is adapted to optically sense said body cavity;
   an irrigation port and a suction port fluidly connected to said lumen of said stem;
   wherein the improvement comprises:
   a cylindrical palm sized enclosure at a proximal end region of said stem, said palm sized enclosure defining a generally uninterrupted smoothly curved, semi-cylindrical lower surface adapted to rest in a palm of an operator and a generally uninterrupted smoothly curved, semi-cylindrical upper surface, a distal end portion of said upper surface forming a resting region for at least one finger of an operator's hand; and
   two flow control valves, respectively controlling suction and irrigation and disposed between corresponding suction and irrigation ports and said stem lumen;

respective operator interface controls, for corresponding control valves, protruding from said uninterrupted semi-cylindrical upper surface;

whereby one or more fingers of said operator have free, unobstructed access to said operator interface controls due to the uninterrupted surfaces of said cylindrical enclosure.

6. An endoscope as claimed in claim 5 wherein the suction control valve is biased in a closed position and the operator interface control is biased upward such that said operator interface control must be depressed to actuate said suction control valve.

7. An endoscope as claimed in claim 5 wherein the diameter of said enclosure plus the height of the respective operator interface controls is such that said endoscope has trumpet-like controls.

8. An endoscope as claimed in claim 5 wherein a forward, top surface of cylindrical enclosure, adjacent and forward of said control valve interfaces, radially slopes towards said stem to provide means for resting non-active fingers of the operator.

9. An endoscope as claimed in claim 1 wherein said palm rest has a forward end region adjacent said proximal end of said stem and a rearward end region opposite said forward end region, said two operator interface controls for said flow valves being vertically disposed above said rearward end region of said palm rest.

10. An endoscope as claimed in claim 1 wherein said palm rest has a rubberized exterior surface.

11. An endoscope as claimed in claim 5 wherein said palm rest has a rubberized exterior surface.

* * * * *